US00PP28120P2

(12) United States Plant Patent
van den Hoogen

(10) Patent No.: US PP28,120 P2
(45) Date of Patent: Jun. 13, 2017

(54) ***HYPERICUM* PLANT NAMED 'ALLMADNE'**

(50) Latin Name: *Hypericum hybrida*
Varietal Denomination: Allmadne

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 14/998,868

(22) Filed: Feb. 23, 2016

(51) Int. Cl.
*A01H 5/02* (2006.01)

(52) U.S. Cl.
USPC ..... Plt./442

(58) Field of Classification Search
USPC ..... Plt./442
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hypericum* plant named 'Allmadne', characterized by its broadly upright plant habit; moderately vigorous growth habit; dark green-colored leaves that are initially greyed red to greyed purple when developing; freely flowering habit and high fruit density; glossy greyed purple to black-colored fruits; and suitability as a garden or container plant.

2 Drawing Sheets

Botanical designation: *Hypericum hybrida.*
Cultivar denomination: 'ALLMADNE'.

BACKGROUND OF THE INVENTION

The present invention relates to a new and distinct cultivar of *Hypericum* plant, botanically known as *Hypericum hybrida*, typically grown as garden or container plant and hereinafter referred to by the name 'Allmadne'.

The new *Hypericum* plant is a product of a planned breeding program conducted by the Inventor in Cuijk, The Netherlands. The objective of the breeding program is to create new *Hypericum* plants with numerous attractive glossy fruits.

The new *Hypericum* plant originated from an open-pollination in September, 2011 in Cuijk, The Netherlands of a proprietary selection of *Hypericum hybrida* identified as code number 11-37-2, not patented, as the female, or seed parent with an unknown selection of *Hypericum hybrida* as the male, or pollen, parent. The new *Hypericum* plant was discovered and selected by the Inventor as a single flowering plant from within the progeny of the stated open-pollination in a controlled outdoor nursery environment in Cuijk, The Netherlands in October, 2012.

Asexual reproduction of the new *Hypericum* plant by vegetative cuttings in a controlled outdoor nursery environment in Cuijk, The Netherlands since October, 2012 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allmadne'. These characteristics in combination distinguish 'Allmadne' as a new and distinct *Hypericum* plant:

1. Broadly upright plant habit.
2. Moderately vigorous growth habit.
3. Dark green-colored leaves that are initially greyed red to greyed purple when developing.
4. Freely flowering habit and high fruit density.
5. Glossy greyed purple to black-colored fruits.
6. Suitable as a garden or container plant.

Plants of the new *Hypericum* differ primarily from plants of the female parent selection in the following characteristics:

1. Plants of the new *Hypericum* and the female parent selection differ in developing leaf color as developing leaves of the female parent selection are green in color.
2. Plants of the new *Hypericum* and the female parent selection differ in fruit color as fruits of the female parent selection are red in color.
3. Fruits of plants of the new *Hypericum* are more rounded in shape than fruits of the female parent selection.

Plants of the new *Hypericum* can be compared to plants of the *Hypericum hybrida* 'Alldiablo', not patented. In side-by-side comparisons conducted in Cuijk, The Netherlands, plants of the new *Hypericum* differ primarily from plants of 'Alldiablo' in the following characteristics:

1. Plants of the new *Hypericum* and 'Alldiablo' differ in fruit color as fruits of 'Alldiablo' are light pink in color.
2. Fruits of plants of the new *Hypericum* are more rounded in shape than fruits of 'Alldiablo'.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph at the top of the first sheet is a side perspective view of a flowering plant of 'Allmadne' grown in a container.

The photograph at the bottom of the first sheet is a close-up view of the upper surface of a typical leaf of 'Allmadne'.

The photograph at the top of the second sheet is a close-up view of typical flowers and developing fruits of 'Allmadne'.

The photograph at the bottom of the second sheet is a close-up view of typical developed fruits of 'Allmadne'.

DETAILED BOTANICAL DESCRIPTION

Plants used for the aforementioned photographs and following description were grown in September in 17-cm containers in an outdoor nursery in Hazerswoude-Dorp, The Netherlands and under cultural practices typical of commercial *Hypericum* production. During the production of the plants, day temperatures ranged from 16° C. to 30° C. and night temperatures ranged from 8° C. to 20° C. Plants were seven months old when the photographs and description were taken. In the following description, color references are made to The Royal Horticultural Society Colour Chart, 2015 Edition, except where general terms of ordinary dictionary significance are used.

Botanical classification: *Hypericum hybrida* 'Allmadne'.

Parentage:

*Female, or seed, parent*.—Proprietary selection of *Hypericum hybrida* identified as code number 11-37-2, not patented.

*Male, or pollen, parent*.—Unknown selection of *Hypericum hybrida*, not patented.

Propagation:

*Type cutting*.—Vegetative cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Perennial shrub; broadly upright plant habit; moderately vigorous growth habit.

*Branching habit*.—Freely basal branching habit, about 18 lateral branches develop per plant.

*Plant height*.—About 33 cm.

*Plant width* (*spread*).—About 34.5 cm.

*Lateral branch description*.—Length: About 14.8 cm. Diameter: About 3 mm. Internode length: About 3.3 cm. Strength: Moderately strong to strong. Texture and luster: Glabrous; glossy. Color, developing: Close to 187B. Color, fully developed: Close to N199C to N199D.

Leaf description:

*Arrangement*.—Opposite, simple; sessile.

*Length*.—About 6.3 cm.

*Width*.—About 3.7 cm.

*Shape*.—Ovate.

*Apex*.—Obtuse.

*Base*.—Truncate to shallowly cordate.

*Margin*.—Entire.

*Texture and luster, upper and lower surfaces*.—Slightly rugose; glabrous; slightly glossy.

*Venation pattern*.—Pinnate.

*Color*.—Developing leaves, upper surface: Darker than between 148A and 152A tinged with close to 183A. Developing leaves, lower surface: Slightly darker than between 178A and 183A. Fully expanded leaves, upper surface: Darker than between 139A and 147A; venation, close to 152A. Fully expanded leaves, lower surface: Close to 147B tinged with close to N77D; venation, close to 175A.

Flower description:

*Flower type, arrangement and flowering habit*.—Single rotate flowers arranged in terminal and axillary compound cymes; freely flowering habit with about nine flowers per cyme and about 165 flowers developing per plant; flowers face mostly upright.

*Fragrance*.—None detected.

*Natural flowering season*.—Plants flower continuously from mid-June to early September in The Netherlands.

*Flower longevity*.—Flowers last about two or three days on the plant; flowers not persistent.

*Fruit longevity* (*postproduction*).—About 30 days.

*Flower buds*.—Length: About 9 mm. Diameter: About 6 mm. Shape: Oblong. Color: Close to 46A; towards the base, close to 153D.

*Inflorescence height*.—About 6.8 cm.

*Inflorescence diameter*.—About 6.3 cm.

*Flower diameter*.—About 2.5 cm.

*Flower depth* (*height*).—About 1.9 cm.

*Petals*.—Quantity and arrangement: Five in a single whorl. Length: About 1.2 cm. Width: About 8 mm. Shape: Ovate to broadly elliptic, concave; strongly reflexed. Apex: Acute, unequal. Base: Attenuate. Margin: Entire. Texture and luster, upper surface: Smooth, glabrous; slightly glossy. Texture and luster, lower surface: Smooth, glabrous; glossy. Color: When opening, upper surface: Close to 17B. When opening, lower surface: Close to 44A; towards the base, close to 12B. Fully opened, upper surface: Close to 15B; color becoming closer to 22A with development. Fully opened, lower surface: Close to 42C to 42D.

*Sepals*.—Quantity and arrangement: Five in a single whorl. Length: About 1.1 cm. Width: About 6 mm. Shape: Broadly ovate; horizontal to slightly reflexed. Apex: Broadly acute. Base: Broadly cuneate. Margin: Entire. Texture and luster, upper and lower surfaces: Smooth, glabrous; matte. Color: When opening, upper surface: Close to 146A strongly tinged with close to 187C. When opening, lower surface: Close to 183C. Fully opened, upper surface: Close to 146A strongly tinged with close to 187C. Fully opened, lower surface: Close to 183A.

*Peduncles*.—Length: About 4.2 cm. Diameter: About 2 mm. Texture: Smooth, glabrous. Strength: Moderately strong. Aspect: Main peduncles, erect; lateral peduncles, about 30° from main peduncles axis. Color: Close to 187C.

*Pedicels*.—Length: About 1.4 cm. Diameter: About 1.5 mm. Texture: Smooth, glabrous. Strength: Moderately strong. Aspect: Main pedicels, erect; lateral pedicels, about 40° from main peduncles axis. Color: Slightly darker than 185A.

*Reproductive organs*.—Stamens: Quantity per flower: About 80. Filament length: About 1.1 mm. Filament color: Close to 23B. Anther length: About 0.5 mm. Anther shape: Broadly oval; dorsifixed. Anther color: Close to 163C. Pollen amount: Scarce. Pollen color: Close to 11A. Pistils: Quantity per flower: Single pistil with three stigmas. Pistil length: About 3.5 mm. Stigma shape: Club-shaped. Stigma color: Close to N186C. Style length: About 3 mm. Style color: Close to 46C to 46D. Ovary color: Close to 20A.

*Fruits*.—Quantity per plant: About 165. Length: About 1.4 cm. Diameter: About 1.3 cm. Shape: Roughly globular. Texture and luster: Smooth, glabrous; glossy. Color: Close to between N186C and 202A; towards the base, close to 185A.

*Seeds*.—Quantity per fruit: About 100. Length: About 0.9 mm. Diameter: About 0.5 mm. Color: Close to 200A.

Disease & pest resistance: Plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Allmadne' as illustrated and described.

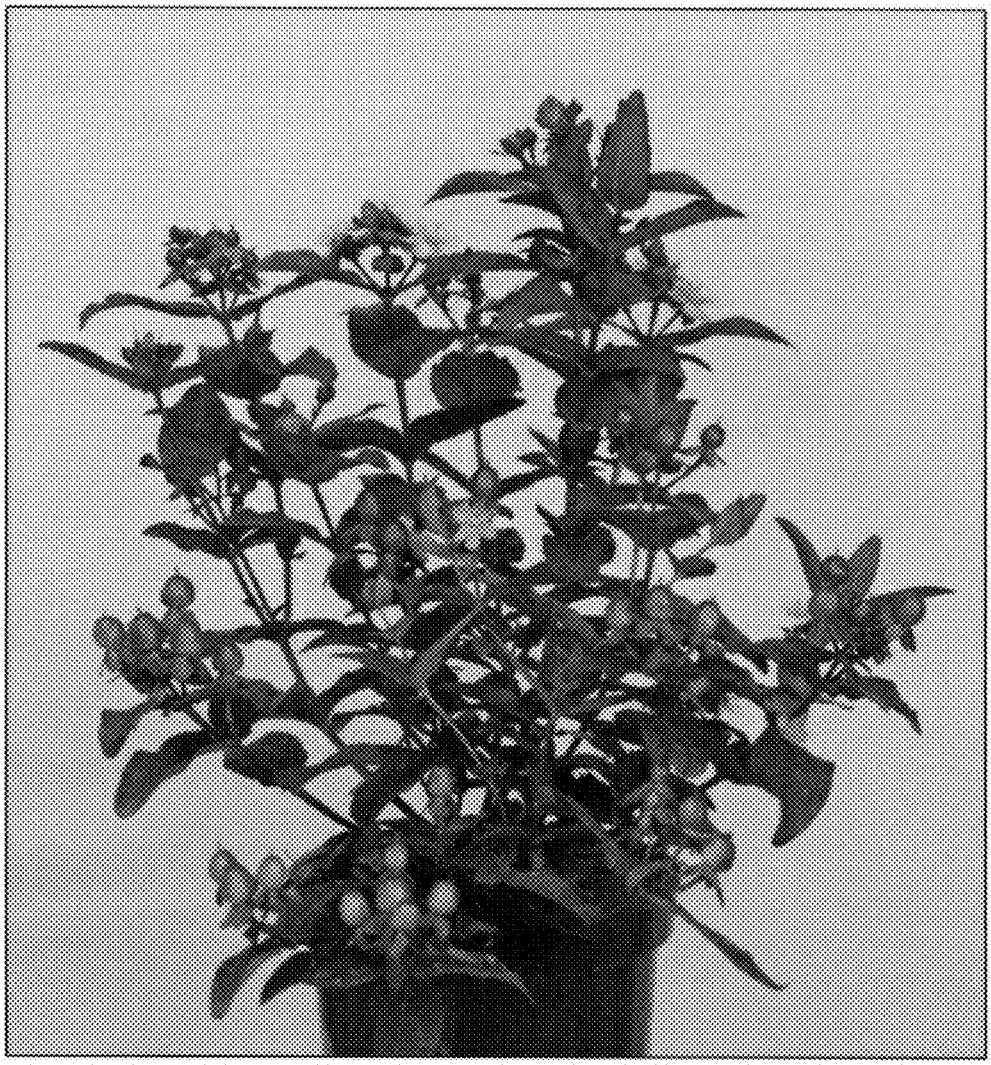
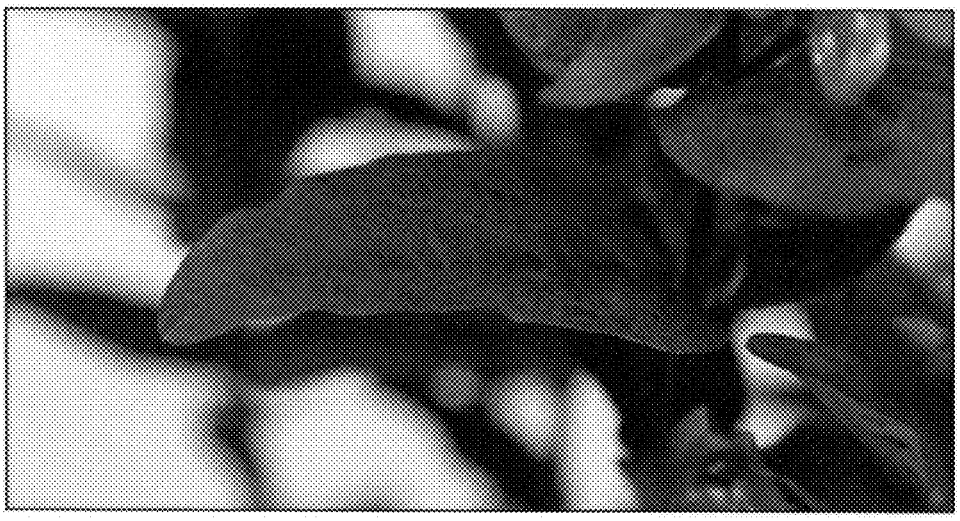

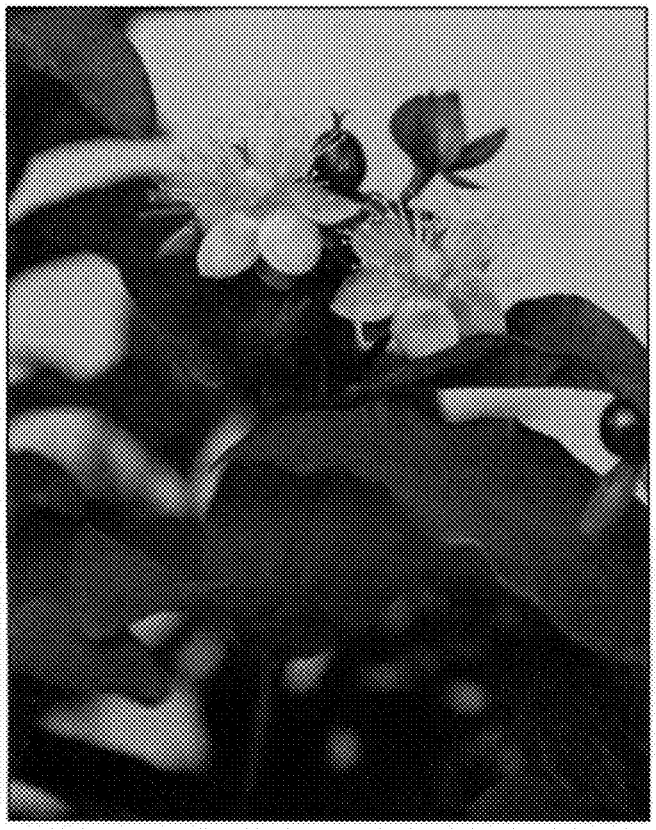
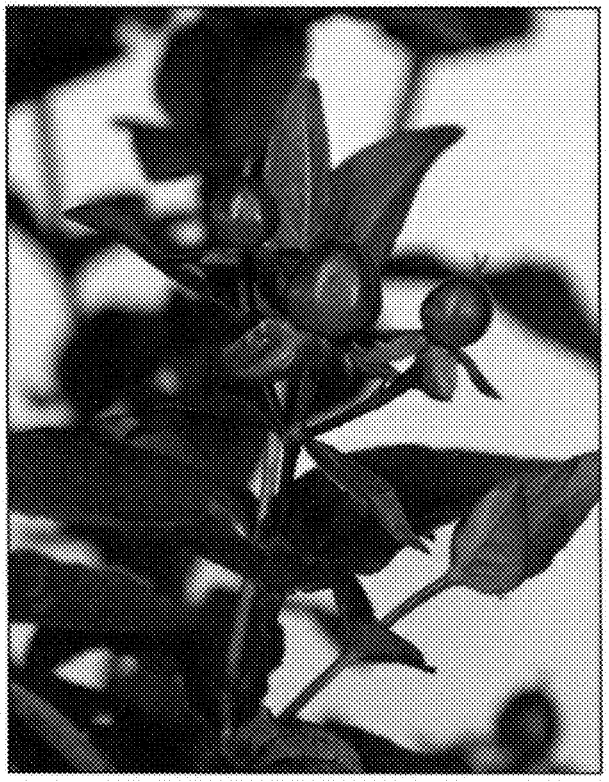

* * * * *